(12) United States Patent
Werner et al.

(10) Patent No.: US 11,808,727 B2
(45) Date of Patent: Nov. 7, 2023

(54) SYSTEMS AND METHODS FOR AN ELECTROCHEMICAL TOTAL CHOLESTEROL TEST

(71) Applicant: Polymer Technology Systems, Inc., Whitestown, IN (US)

(72) Inventors: Brittney Werner, Beech Grove, IN (US); Aniruddha Patwardhan, Fishers, IN (US); Gary Hughes, Camby, IN (US)

(73) Assignee: Polymer Technology Systems, Inc., Whitestown, IN (US)

( * ) Notice: Subject to any disclaimer, the term of this patent is extended or adjusted under 35 U.S.C. 154(b) by 0 days.

(21) Appl. No.: 15/670,499

(22) Filed: Aug. 7, 2017

(65) Prior Publication Data

US 2019/0011389 A1 Jan. 10, 2019

Related U.S. Application Data

(60) Provisional application No. 62/529,286, filed on Jul. 6, 2017.

(51) Int. Cl.
*G01N 27/327* (2006.01)
*C12Q 1/00* (2006.01)

(52) U.S. Cl.
CPC ......... *G01N 27/3272* (2013.01); *C12Q 1/005* (2013.01); *C12Y 101/03006* (2013.01);
(Continued)

(58) Field of Classification Search
CPC ........... G01N 27/3272; G01N 27/3273; G01N 2333/904; G01N 27/3275; C12Y 101/03006; C12Q 1/005
See application file for complete search history.

(56) References Cited

U.S. PATENT DOCUMENTS

2004/0106190 A1 6/2004 Yang et al.
2005/0072670 A1\* 4/2005 Hasegawa .......... G01N 27/3272
204/403.01
(Continued)

OTHER PUBLICATIONS

International Search Report and Written Opinion dated Oct. 30, 2017 issued in related PCT App. No. PCT/US2017/045718 (12 pages).

(Continued)

*Primary Examiner* — Mayla Gonzalez Ramos
(74) *Attorney, Agent, or Firm* — Haynes and Boone, LLP

(57) ABSTRACT

An electrochemical test for total cholesterol includes a test strip for an electrochemical testing testing of a blood analyte which includes a first receiving port, the first receiving port for receiving a blood sample, the first receiving port at a first end of the test strip. The test strip further includes a first electrode and a second electrode, the first and second electrodes proximate to the first receiving port. The test strip further includes a first contact and a second contact, the first and second contacts at a second end of the test strip, the first and second contacts interconnected with the first and second electrodes, respectively. The test strip further includes cholesterol oxidase, located proximate to the first and the second electrode. The test strip further includes a mediator, located proximate to the first and the second electrode, wherein the cholesterol oxidase and the mediator interact with the blood sample and the first and second electrode to generate a measurable electrical event.

7 Claims, 5 Drawing Sheets

(52) U.S. Cl.
CPC ..... *G01N 27/3273* (2013.01); *G01N 27/3275* (2013.01); *G01N 2333/904* (2013.01)

(56) References Cited

U.S. PATENT DOCUMENTS

| | | | |
|---|---|---|---|
| 2005/0221502 A1* | 10/2005 | Shindelman | G01N 33/92 436/514 |
| 2009/0008248 A1 | 1/2009 | Shimomura et al. | |
| 2011/0155590 A1 | 6/2011 | Huffstodt et al. | |
| 2013/0020196 A1 | 1/2013 | Nishiwaki et al. | |
| 2015/0027886 A1* | 1/2015 | Takagi | G01N 27/327 204/403.14 |
| 2015/0104847 A1* | 4/2015 | Aratake | C12N 9/96 435/188 |
| 2016/0355862 A1* | 12/2016 | Deng | C12Q 1/006 |

OTHER PUBLICATIONS

Volonte et al., "Production of recombinant cholesterol oxidase containing covalently bound FAD in *Escherichia coli*," BMC Biotechnology 2010, vol. 10, Issue 33, pp. 1-10 (10 pages).

"Cholesterol Esterase," Roche CustomBiotech Catalog, 15$^{th}$ Edition: Clinical Chemistry and Immunology, May 1, 2017 (May 1, 2017), pp. 67-74. Retrieved from the Internet: http://custombiotech.roche.com/content/dam/internet/dia/custombiotech/custombiotech_com/en_GB/pdf/CustomBiotech_catalog_Clinical_Chemistry_Immunolgy_2017.pdf on Sep. 27, 2017 (Sep. 27, 2017), entire document.

* cited by examiner

SYSTEMS AND METHODS FOR AN ELECTROCHEMICAL TOTAL CHOLESTEROL TEST

CROSS-REFERENCE TO RELATED APPLICATION

This application claims the benefit of U.S. Provisional Application No. 62/529,286, filed on Jul. 6, 2017, which is incorporated herein by reference in its entirety.

BACKGROUND

Point of Care ("POC") and home testing for various blood analytes and other detectable metrics in bodily fluids is desirable for patient and doctor. Two primary types of test strips are available for testing for blood analytes. These test strips include electrochemical and optical test strips. Optical test strips rely on a color change reaction resulting from the presence of an analyte. A light then is shone on the test strip and an optical feature of the test strip then is measured. Optical features include, but are not limited to, reflectance, absorption, and color. In an electrochemical test strip, a voltage, amperage, capacitance, or other electric feature is measured by two or more electrodes that contact the sample. In many scenarios, the test strips may include printed circuit pathways and reagent coatings on the two or more electrodes. Generally, it is thought that electrochemical strips are less expensive to manufacture and are generally thought to be more reliable. However, electrochemical strips have not generally been adapted to include multiple tests.

The CardioChek platform offers a reflectance based cholesterol test. This test relies on several membranes. Finding a method to electrochemically measure cholesterol will allow us to eliminate dependence on membranes while also improving precision, accuracy and speed. The membrane market for reflectance testing has been diminishing and inconsistent, therefore electrochemical testing is a fast rising field. Being able to measure cholesterol fast and accurately through electrochemical testing will be of great benefit.

BRIEF SUMMARY

In one embodiment, a test strip for electrochemical testing of a blood analyte includes a first receiving port, the first receiving port for receiving a blood sample, the first receiving port at a first end of the test strip. The test strip further includes a first electrode and a second electrode, the first and second electrodes proximate to the first receiving port. The test strip further includes a first contact and a second contact, the first and second contacts at a second end of the test strip, the first and second contacts interconnected with the first and second electrodes, respectively. The test strip further includes cholesterol oxidase, located proximate to the first and the second electrode. The test strip further includes a mediator, located proximate to the first and the second electrode, wherein the cholesterol oxidase and the mediator interact with the blood sample and the first and second electrode to generate a measurable electrical event. (Optionally, one of the first and second electrodes includes the cholesterol esterase and the mediator on a surface of one of the first and second electrodes.) Alternatively, the cholesterol oxidase and the mediator is painted on to the one of the first and second electrodes. In one alternative, the mediator is an osmium compound. In another alternative, the mediator is ferricyanide. (Optionally, the cholesterol oxidase is Microorganism recombinant 11479709103.)

In one embodiment, a test strip system for electrochemical testing of a blood analyte includes a first receiving port, the first receiving port for receiving a blood sample, the first receiving port at a first end of the test strip. The system further includes a first electrode and a second electrode, the first and second electrodes proximate to the first receiving port. The system further includes a first contact and a second contact, the first and second contacts at a second end of the test strip, the first and second contacts interconnected with the first and second electrodes, respectively. The system further includes cholesterol oxidase, located in a premix device. The system further includes a mediator, located in a premix device, wherein the blood sample is placed in the premix device and after mixing the blood sample is dosed on the first receiving port and the cholesterol oxidase and the mediator interact with the blood sample and the first and second electrode to generate a measurable electrical event. Optionally, the mediator is an osmium compound. Alternatively, the mediator is ferricyanide. In one alternative, the cholesterol oxidase is Microorganism recombinant 11479709103. Optionally, the premix device further includes a surfactant solution. Alternatively, the surfactant solution includes Triton X-100, Sodium Cholate, Potassium Phosphate, cholesterol esterase, cholesterol oxidase, and BSA. In one alternative, the mediator is an osmium compound and the cholesterol oxidase is Microorganism recombinant 11479709103.

In one embodiment, a test strip and meter combination system for electrochemical testing of a blood analyte includes a test strip including a first receiving port, the first receiving port for receiving a blood sample, the first receiving port at a first end of the test strip. The test strip further includes a first electrode and a second electrode, the first and second electrodes proximate to the first receiving port. The test strip further include a first contact and a second contact, the first and second contacts at a second end of the test strip, the first and second contacts interconnected with the first and second electrodes, respectively. The system further includes a meter, the meter having a test strip receiving port shaped to receive the test strip, the meter including a plurality of contacts, a first portion of the plurality of contacts positioned to interface with the first and second contacts. The system further includes a mediator and cholesterol oxidase for interacting with the blood sample and the first and second electrode to produce a cholesterol level measured on the basis of a measurable electrical event detected by the meter and converted to the cholesterol level. Optionally, the mediator is an osmium compound. Alternatively, the mediator is ferricyanide. In one configuration, the cholesterol oxidase is Microorganism recombinant 11479709103. In one alternative, comprising a premix device, wherein the premix device includes the cholesterol oxidase, the mediator, and a surfactant solution. Optionally, the surfactant solution includes Triton X-100, Sodium Cholate, Potassium Phosphate, cholesterol esterase, cholesterol oxidase, and BSA. Alternatively, the mediator is an osmium compound and the cholesterol oxidase is Microorganism recombinant 11479709103.

DETAILED DESCRIPTION

Figure 1:
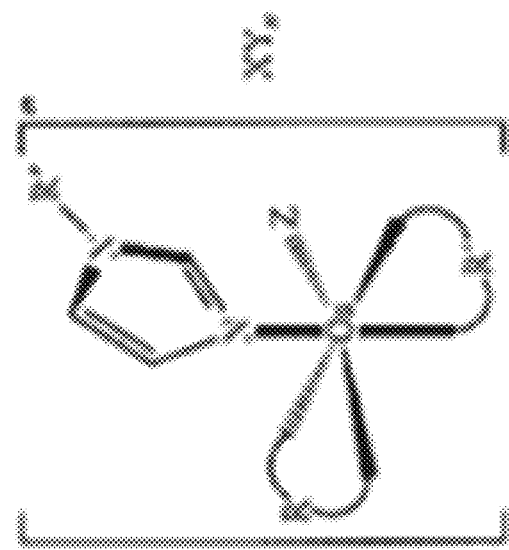
FIG. 1 shows one embodiment of an osmium compound that may be used as a mediator in the presently described system.

Certain terminology is used herein for convenience only and is not to be taken as a limitation on the embodiments of the systems and methods for an electrochemical cholesterol test strip. In the drawings, the same reference letters are employed for designating the same elements throughout the several figures. Embodiments of the electrochemical test strips may fit with a standardized meter that may equally receive strips that have a single sample and set of electrodes and strips that have multiple analytes.

Embodiments of an electrochemical cholesterol test strip are described herein. Advantages of the electrochemical test strip include:
1. Being able to measure total cholesterol electrochemically eliminates dependence on membranes while also improving precision, accuracy, and speed.
2. Electrochemical total cholesterol testing requires much less blood volume (2 μL vs. 15 μL).
3. Electrochemical sensors require much less reagent compared to reflectance testing, making the cost much cheaper. Cost is also reduced by not using membranes.
4. An electrochemical total cholesterol approach is an advantage because it allows PTS to be less dependent on the diminishing and inconsistent membrane market.

With the advent of the electrochemical glucose assay, it has been the desire of many to create other electrochemical assays because of the before mentioned advantages. Unfortunately, not all electrochemical reactions are as simple as glucose. An electrochemical reaction must use the appropriate enzymes and mediator. Embodiments described herein, have demonstrated proof of concept of an electrochemical cholesterol reaction.

The reaction mechanism for measuring cholesterol using an enzymatic pathway is disclosed herein. In many embodiments, the enzymatic path to measuring cholesterol is relatively straight forward. It begins with using an esterase to hydrolyze cholesterol esters to obtain unesterified cholesterol and fatty acid. The reaction is seen below in equation 1:

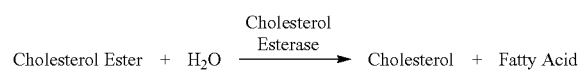

eq 1

Once the cholesterol esterase hydrolyzes the cholesterol esters, cholesterol oxidase can then act upon the unesterified cholesterol in the presence of a mediator and yield oxidized cholesterol and a reduced mediator. The cholesterol oxidase will transfer electrons directly to the mediator as shown in the reaction below in equation 2:

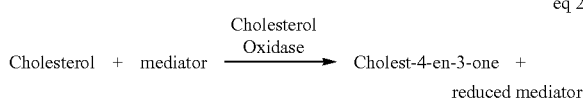

eq 2

The reduced mediator may then creates an electric potential, current, or other measurable electrical event. Those skilled in the art of electrochemistry will realize that not all cholesterol oxidases will transfer electrons to a mediator, nor will all mediators work with preferred cholesterol oxidases. Mediators and cholesterol oxidases may be suggested in the prior art but cannot be utilized effectively without significant experimentation. Numerous cholesterol oxidases and several mediators have been tested and manipulated and embodiments described herein present a cholesterol oxidase and mediator system that works well.

Figure 2:
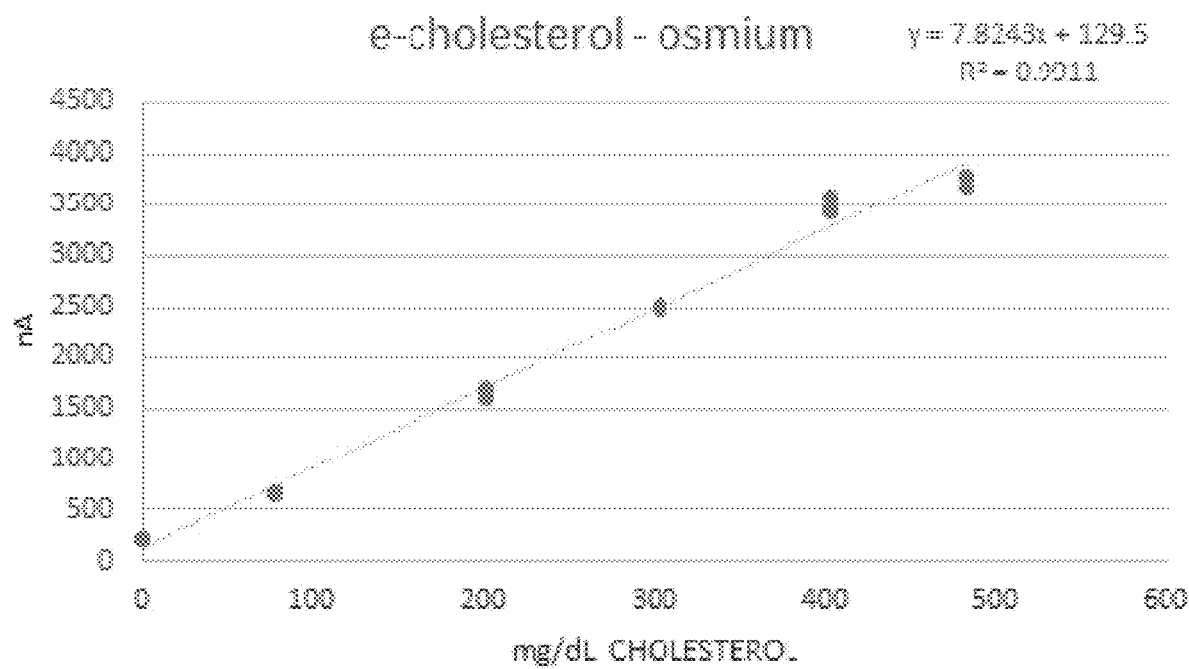
FIG. 2 shows one embodiment of a graph of the reaction of spiked cholesterol plasma samples with cholesterol oxidase using different mediators.

Roche's cholesterol oxidase (microorganism recombinant 11479709103) is a preferred enzyme for the reaction above. The osmium compound, shown in FIG. 1, is the preferred mediator. In addition, we have found that other mediators may also be used, such as ferricyanide shown in FIG. 2. Many other cholesterol oxidase enzymes (Table 1) that were screened displayed much less or no ability to transfer electrons to a mediator. Table 1 shows various mediators and enzymes tested. Other possible mediators include ruthenium, phenazine ethosulphate, phenazine methosulfate, pheylenediamine, 1-methoxy-phenazine methosulfate, 2,6-dimethyl-1,4-benzoquinone, 2,5-dichloro-1,4-benzoquinone, indophenols, osmium bipyridyl complexes, tetrathiafulvalene, phenanonthroline quinone, and ferricyanide.

FIG. 1 shows an example of an osmium compound that may be used as a mediator in the presently described system. Various R groups may be utilized in the compound, for example: R and R' are the same or different and are selected from 2,2'-bipyridyl, 4-4'-disubstituted-2,2'-bipyridyl, 5,5'-disubstituted-2,2'-bipyridyl, 1,10-phenanthrolinyl, 4-7-disubstituted-1,10-phenanthrolinyl, and 5,6-disubstituted-1,10-phenanthrolinyl, wherein the disubstitution is a methyl, ethyl, or phenyl group. R and R' are coordinated to osmium at their nitrogen atoms and R" is selected from hydrogen, methyl, and ethyl.

Figure 4:
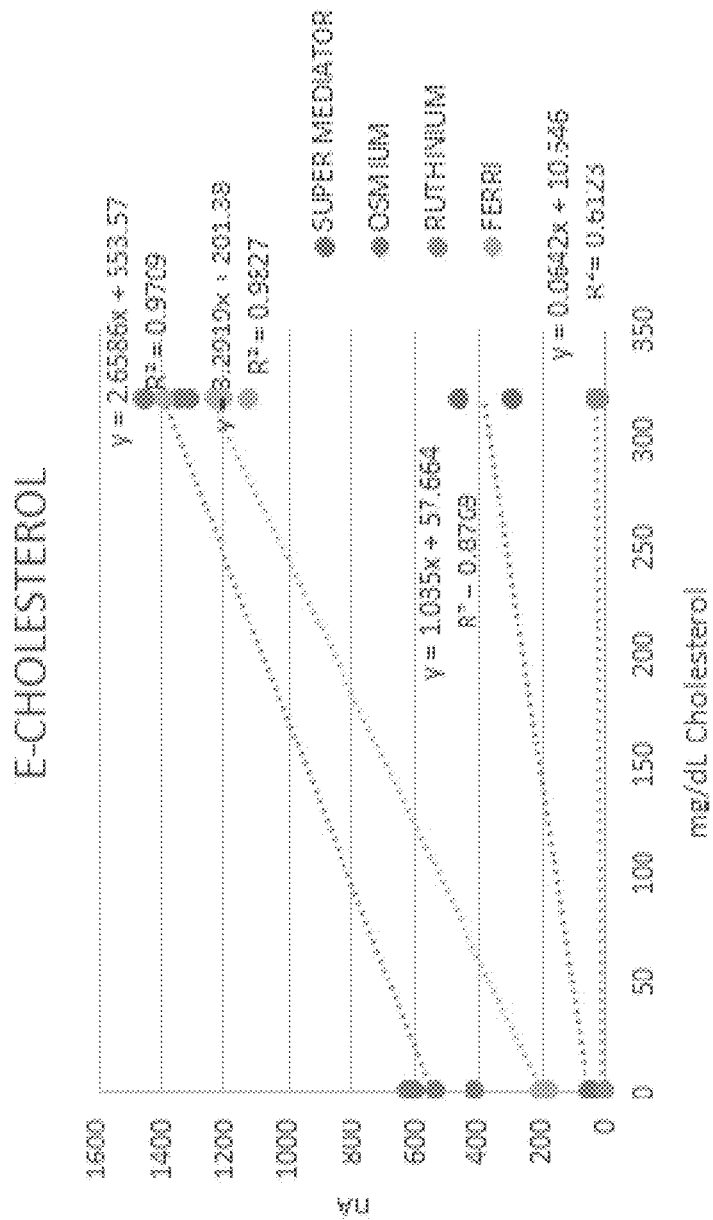
FIG. 4 shows a graph of nA verses total cholesterol level as determined experimentally with an embodiment of the systems described herein.

FIG. 4 shows the reaction of spiked cholesterol plasma samples with cholesterol oxidase using different mediators. The sensors were carbon electrodes. In FIG. 4 the slope of the data is shown as well as the R squared values. As shown in the graph, the use of osmium as a mediator, appears to have a high R squared value. Additionally, the osmium mediator has a higher y intercept than a ferricyanide mediator, and therefore may be easier for the meter to measure. Osmium is shown in the top most graph line, ferricyanide in the next line down, a super mediator next, and finally ruthenium. The super mediator is a combination between osmium and ruthenium compounds.

TABLE 1

Cholesterol Oxidases screened for electrochemical total cholesterol.

| Vendor | Cholesterol Oxidase Lot # | Dose Response |
|---|---|---|
| Roche | Microorganism recombinant 11479709103 | Yes |
| Roche | *Streptomyces* species 10634522103 | Slight |
| Toyobo | COO-331 | No |
| Toyobo | COO-311 | No |
| Toyobo | COO-321 | No |

Embodiments and examples described herein shown proof of concept that cholesterol esterase will hydrolyze cholesterol esters allowing cholesterol oxidase to then react and directly transfer electrons to the osmium mediator.

Figure 3:
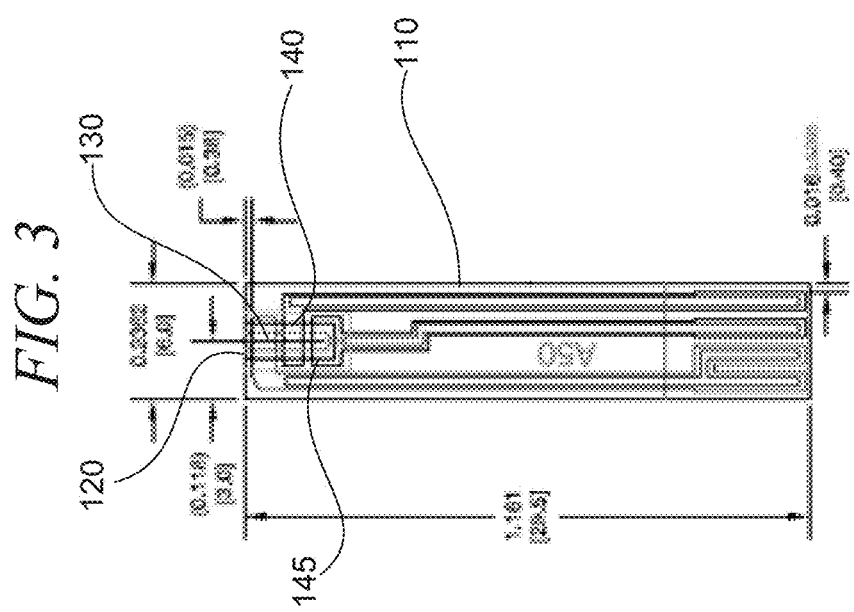
FIG. 3 shows an exemplary test strip system.
Figure 5:
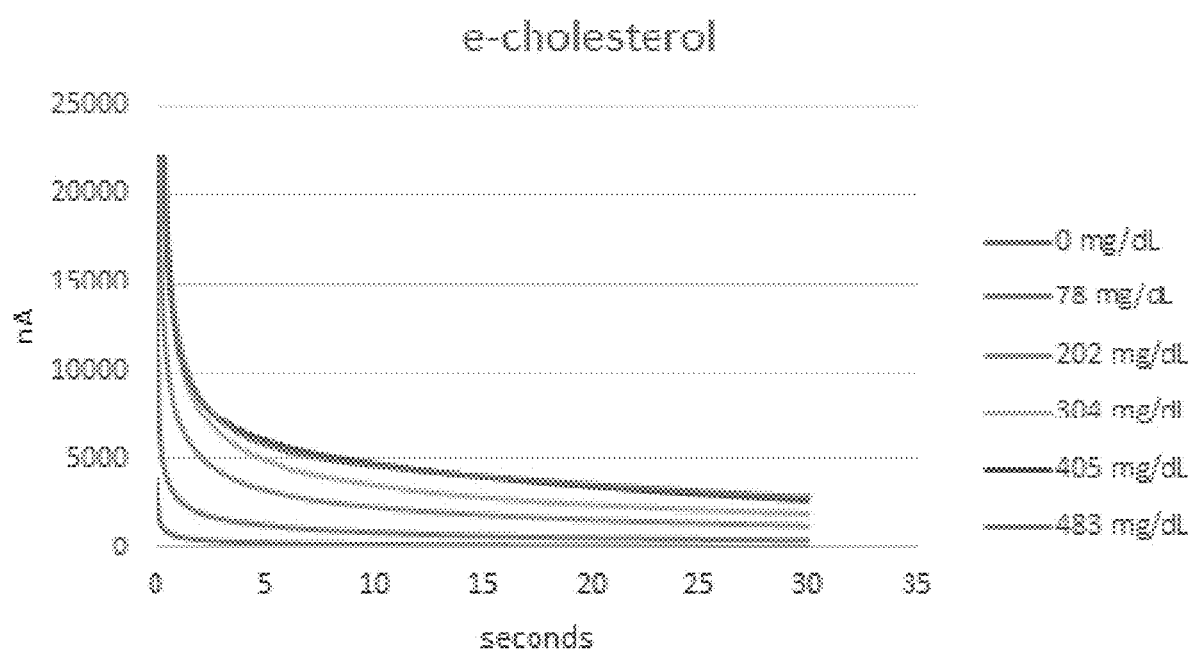
FIG. 5 shows a graph of the nA verses time to show where various total cholesterol levels in a sample more or less reach steady state.

In one embodiment, a surfactant solution is provided, listed in Table 2, containing the osmium mediator and enzymes. The surfactant solution was mixed in a 1:1 ratio with cholesterol plasma samples. The reagent/plasma solution was dosed on blank carbon electrodes (displayed in FIG. 3) to generate the signal. As shown in FIG. 3, the test strip includes a test strip body 110, a sample channel 120, a fill detector electrode 130, and a first and second electrode 140, 145. This is only one possible schematic for the test strip. A potential of +250 mV was applied. As demonstrated by FIG. 4 and FIG. 5, a good dose response was acquired that covered the entire dynamic range of cholesterol (100-400 mg/dL), along with an excellent correlation of 0.991 indicating an efficient transfer of electrons to the mediator and to the electrode.

In one embodiment, an electrochemical test strip system may include a premix device for receiving a sample, the premix device providing for dosing of an electrochemical strip. The premix device may include a surfactant solution that mixes with sample to create a premixed sample. The system may further include an electrochemical test strip for receiving a dose of sample from the premix device. The electrochemical test strip may be inserted into a meter and the meter measures the current provided by the sample interacting with the electrodes of the system. Alternatively, the meter may measure the voltage created by the sample interacting with the electrodes of the test strip. In one alternative, the system may not include a premix step. Instead the surfactant solution may be dried, plated, sprayed, or otherwise applied to one or more electrodes of the electrochemical test strip. In operation the sample may mix with the dried surfactant solution and then create an electrical current or voltage in relation to the electrodes of the system, In another alternative, the test strip may include a capillary tube at the application site, whereby the capillary tube leads to the electrode area. In the capillary tube, dried surfactant solution may be located, whereby the surfactant solution is wetted by the sample and then provided for interaction with the electrodes as described above. In an alternative, the capillary tube may be sealed prior to application of the sample and may contain a surfactant solution. Upon addition of the sample the surfactant solution may interact with the sample, thereby causing the sample/surfactant solution to interact with the electrodes and yield an electrical voltage or current.

Additionally, it is noted that in some scenarios it may be desirable to remove hematocrit prior to the testing of the sample. This may be accomplished via a blood separation membrane, tested with various materials such as coagulants (such as lectins) or other chemistry that assists in blood separation. The blood separation membrane may be placed above a sample window or in a capillary tube as described above.

TABLE 2

Surfactant solution used in a 1:1 ratio with spiked cholesterol plasma samples.
Surfactant Solution - pH 7.5

| | |
|---|---|
| Triton X-100 | 0.2% |
| Sodium Cholate | 4.0% |
| K Phosphate | 50 mmol/L |
| Osmium | 100 mmol/L |
| Cholesterol Esterase | 200 KU/L |
| Cholesterol Oxidase | 200 KU/L |
| BSA | 2% |

There are numerous potential advantages of providing an electrochemical platform, as described above, and additionally 1) the calibration of meters is standardized to generally measure nano amps (nA) and microchips exist that are self-calibrating; 2) electrochemical systems such as this are generally more energy efficient than optical systems, requiring less battery power; 3) the systems are generally more precise; and 4) the testing sites may potentially be panelized, thus providing multiple tests per test strip.

In conclusion, embodiments of an electrochemical test strip are provided that will allow for cholesterol testing. The meter is generally programed to detect and receive a test strip, run an algorithm to test a voltage or current and determine a cholesterol level in a sample.

In many embodiments, parts of the system, especially the meter, are provided in devices including microprocessors. Various embodiments of the systems and methods described herein may be implemented fully or partially in software and/or firmware. This software and/or firmware may take the form of instructions contained in or on a non-transitory computer-readable storage medium. Those instructions then may be read and executed by one or more processors to enable performance of the operations described herein. The instructions may be in any suitable form such as, but not limited to, source code, compiled code, interpreted code, executable code, static code, dynamic code, and the like. Such a computer-readable medium may include any tangible non-transitory medium for storing information in a form readable by one or more computers such as, but not limited to, read only memory (ROM); random access memory (RAM); magnetic disk storage media; optical storage media; a flash memory, etc.

Embodiments of the systems and methods described herein may be implemented in a variety of systems including, but not limited to, smartphones, tablets, laptops, and combinations of computing devices and cloud computing resources. For instance, portions of the operations may occur in one device, and other operations may occur at a remote location, such as a remote server or servers. For instance, the collection of the data may occur at a smartphone, and the data analysis may occur at a server or in a cloud computing resource. Any single computing device or combination of computing devices may execute the methods described.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof.

What is claimed as new and desired to be protected by Letters Patent of the United States is:

1. A dry test strip for electrochemical testing of a blood analyte, the test strip comprising:
   a first receiving port, the first receiving port for receiving a blood sample, the first receiving port at a first end of the test strip, wherein a blood separation membrane is placed over the first receiving port, the blood separation membrane including lectins;
   a first electrode and a second electrode, the first and second electrodes proximate to the first receiving port, including a capillary tube at the first receiving port, wherein the capillary tube leads to the first electrode and the second electrode and in the capillary tube, a dried surfactant solution is located, whereby the dried surfactant solution is wetted by the blood sample;

a first contact and a second contact, the first and second contacts at a second end of the test strip, the first and second contacts interconnected with the first and second electrodes, respectively;

cholesterol oxidase, located proximate to the first and the second electrode;

a mediator, located proximate to the first and the second electrode, wherein the cholesterol oxidase and the mediator interact with the blood sample and the first and second electrode to generate a measurable electrical event, wherein the cholesterol oxidase is configured such that the cholesterol oxidase reacts and directly transfer electrons to the mediator such that mediator interacts with the first and second electrode, wherein the mediator is an osmium compound;

the dried surfactant solution including Sodium Cholate, Potassium Phosphate, and BSA (bovine serum alluvium), located proximate to the first and second electrode.

2. The test strip of claim 1, wherein one of the first and second electrodes includes the cholesterol oxidase and the mediator on a surface of one of the first and second electrodes.

3. The test strip of claim 2, wherein the cholesterol oxidase and the mediator is painted on to the one of the first and second electrodes.

4. The test strip of claim 1, wherein the cholesterol oxidase is Microorganism recombinant 11479709103.

5. A dry test strip and meter combination system for electrochemical testing of a blood analyte, the system comprising:

a dry test strip including:

a first receiving port, the first receiving port for receiving a blood sample, the first receiving port at a first end of the test strip, wherein a blood separation membrane is placed over the first receiving port, the blood separation membrane including lectins;

a first electrode and a second electrode, the first and second electrodes proximate to the first receiving port, including a capillary tube at the first receiving port, wherein the capillary tube leads to the first electrode and the second electrode and in the capillary tube, a dried surfactant solution is located, whereby the dried surfactant solution is wetted by the blood sample;

a first contact and a second contact, the first and second contacts at a second end of the test strip, the first and second contacts interconnected with the first and second electrodes, respectively;

a meter, the meter having a test strip receiving port shaped to receive the test strip, the meter including a plurality of contacts, a first portion of the plurality of contacts positioned to interface with the first and second contacts; and a mediator and cholesterol oxidase configured to interact with the blood sample and the first and second electrode to produce a cholesterol level measured on the basis of a measurable electrical event detected by the meter and converted to the cholesterol level, wherein the mediator is an osmium compound;

the dried surfactant solution including Sodium Cholate, Potassium Phosphate, and BSA (bovine serum alluvium), located proximate to the first and second electrode.

6. The test strip and meter combination system of claim 5, wherein the cholesterol oxidase is Microorganism recombinant 11479709103.

7. The test strip of claim 5, wherein the mediator is an osmium compound and the cholesterol oxidase is Microorganism recombinant 11479709103, the combination resulting in a high R squared value a higher y intercept than a ferricyanide mediator.

* * * * *